(12) United States Patent
Wiggenhauser et al.

(10) Patent No.: US 7,587,943 B2
(45) Date of Patent: Sep. 15, 2009

(54) DEVICE FOR THE DESTRUCTION-FREE TESTING OF COMPONENTS

(75) Inventors: Herbert Wiggenhauser, Berlin (DE); Andrey A. Samokrutov, Moskau (RU)

(73) Assignees: BAM Bundesanstalt fur Materialforschung und-prufung, Berlin (DE); Acoustic Control Systems, Moskau (RU)

( * ) Notice: Subject to any disclaimer, the term of this patent is extended or adjusted under 35 U.S.C. 154(b) by 93 days.

(21) Appl. No.: 11/764,937

(22) Filed: Jun. 19, 2007

(65) Prior Publication Data
US 2008/0110264 A1    May 15, 2008

(30) Foreign Application Priority Data
Jun. 20, 2006    (DE)    .................. 10 2006 029 435

(51) Int. Cl.
G01N 29/26    (2006.01)
A61B 8/00    (2006.01)
(52) U.S. Cl. .................. 73/625; 73/628; 600/437
(58) Field of Classification Search .................. 73/625, 73/626, 628, 583, 640, 641, 644; 600/437, 600/443, 447, 456, 458; 128/916
See application file for complete search history.

(56) References Cited

U.S. PATENT DOCUMENTS

| | | | | |
|---|---|---|---|---|
| 4,545,251 A * | 10/1985 | Uchida et al. | .................. | 73/631 |
| 5,067,352 A | 11/1991 | Floret | | |
| 5,251,631 A * | 10/1993 | Tsuchiko et al. | ............ | 600/447 |
| 5,628,319 A * | 5/1997 | Koch et al. | ................... | 600/437 |
| 5,893,832 A * | 4/1999 | Song | .......................... | 600/443 |
| 6,120,449 A * | 9/2000 | Snyder et al. | ............... | 600/447 |
| 6,186,006 B1 | 2/2001 | Schmitz | | |
| 6,279,399 B1 * | 8/2001 | Holm | .......................... | 73/626 |
| 6,500,126 B1 * | 12/2002 | Brock-Fisher | .............. | 600/459 |
| 6,957,583 B2 | 10/2005 | Tooma et al. | | |
| 7,207,940 B2 | 4/2007 | Sato | | |
| 7,369,458 B2 * | 5/2008 | Sifferman et al. | ............. | 367/13 |

FOREIGN PATENT DOCUMENTS

| | | |
|---|---|---|
| DE | 69005684 T2 | 7/1994 |
| DE | 19633813 C2 | 2/1998 |
| EP | 1415731 A2 | 5/2004 |
| JP | 2004174227 | 6/2004 |
| RU | 2080592 C1 | 5/1997 |

OTHER PUBLICATIONS

German Examination Report of Patent Application 102006029435. 1-52.

* cited by examiner

*Primary Examiner*—J M Saint Surin
(74) *Attorney, Agent, or Firm*—Matthew B. Dernier, Esq.; Gibson & Dernier LLP

(57) ABSTRACT

A device for the destruction-free testing of components, in particular of concrete components with ultrasound is suggested, which comprises at least one sensor module with several ultrasonic testing heads functioning as transmitters and/or receivers. The sensor module is provided with a device for producing transmitter impulses for the ultrasonic radiation and with a device for acquiring the readings. Several sensor modules for forming an array are mechanically connected to one another. Furthermore, a control- and evaluation device for activating the sensor modules with their ultrasonic heads and for evaluation of the readings delivered by the sensor modules is provided, which via a bus system is connected with control- and data leads to the sensor modules.

12 Claims, 2 Drawing Sheets

DEVICE FOR THE DESTRUCTION-FREE TESTING OF COMPONENTS

FIELD OF THE INVENTION

The invention relates to a device for the destruction-free testing of components, in particular concrete components, with ultrasound, according to the introductory part of the main claim.

BACKGROUND OF THE INVENTION

The inner structure of steel-concrete components, given access to only one side, may only be examined with a significant technical effort and a great expense with regard to time. The essential methods for this are radar, as well as the ultrasonic-pulse-echo methods. Common to both methods is the fact that these only permit imaged representations of the inside of the examined concrete components with multiple measurements and an extensive processing thereafter.

An ultrasonic device for the inspection of fractures or likewise is known from EP 1 415 731 A2, and this comprises a sensor with several ultrasonic elements and ultrasonic receiver elements, wherein fractures are detected on account of the received scatter echo signals.

Furthermore, an ultrasonic array with ultrasonic testing heads arranged in parallel, with ceramic tips and a resilient holder is described in RU 2 080 592 C1, wherein a part of the ultrasonic array represents transmitter elements, and a part represents receiver elements.

SUMMARY OF THE INVENTION

It is the object of the invention to provide a rapid and automatically functioning, destruction-free data acquisition and testing of components, in particular concrete components, with ultrasound, wherein a multitude of readings are to be made available for evaluation.

According to the invention, this object is achieved by the features in the latter part of the main claim in combination with the features of the introductory part.

By way of the fact that several sensor modules, in each case with a plurality of ultrasonic testing heads for forming an array are mechanically connected to one another, and that a control- and evaluation device for activating the sensor modules with their ultrasonic heads and for evaluating the measurement data provided by the sensor modules, is connected to the sensor modules via a bus system with control- and data leads, one ensures a parallel acquisition of data and a very rapid data transmission after the effected measurement, with which an imaged reconstruction of the component is made possible with the help of the SAFT (synthetic aperture focusing technique) algorithm, Advantageous further formations and improvements are possible by way of the measures provided in the dependent claims.

The testing heads of each sensor module are advantageously individually mounted in resilient holders, and provided with contacts, preferably ceramic tips, wherein the resilient holders ensure that all testing heads gave a good contact, even to a coarse surface of the object being examined. In an advantageous manner, the testing heads of each sensor module are linearly arranged in a row and is accommodated in a module housing, wherein the sensor modules by way of a holder, preferably a plug connection, are mechanically and/or electrically connected to one another into an array, in a releasable manner. By way of this, modules may be supplemented or removed at any time, so that the array may be adapted to the measurement task in a simple manner. At least two sensor modules are necessary for the construction of a linear array, as a rule it is at least 10, maximally about 25 sensor modules. By way of this arrangement of the sensor modules with in each case, for example four ultrasonic testing heads which are arranged parallel in a row, there results a rectification effect of the ultrasound signal and a significantly improved signal shape and high intensity in the examination region.

It is particularly advantageous that the control- and evaluation device is designed in a manner such that it recognizes the respective sensor module on joining together into the array, and configures and activates it as a transmitter- or receiver sensor. This is particularly advantageous, since no adaptation work is necessary when modules are added or removed. The control- and evaluation device designed as a base apparatus, via the bus system, may configure each sensor module independently, for example as a transmitter module, wherein then all other modules are automatically receiver modules, which record measurement data in a parallel manner. The testing heads advantageously produce ultrasonic transversal waves, but testing heads with longitudinal waves may also be used. Additionally, one may also provide testing heads with selectable polarization direction of the transversal waves and/or a switch-over between longitudinal- and transversal operation. It is advantageous for the control- and evaluation device to generate a start signal for the beginning of a measurement sequence via the data bus to the sensor modules, wherein each measurement sequence selects a module as a transmitter, and reads out the received data from the other modules. Infinitely many repetitions of the measurements may take place within each sequence, for improving the signal-to-noise ratio.

Advantageously, the electronics for the testing heads of a sensor module are integrated in the housing of the sensor module, by which means the sensor module is insensitive to electromagnetic disturbances. Thereby, the electronics advantageously consist of an amplifier, of an AD-transducer and a memory, wherein the received data of a measurement sequence which is detected and converted by the testing heads serving as receivers, is stored in the memory.

In an advantageous manner, the measurement data from the sensor modules is transmitted from the control- and evaluation device of the base apparatus to this, after the measurement or after each measurement sequence, and a new measurement sequence may begin.

The selected measurement data may be transmitted to different peripheral apparatus by way of the provision of interfaces on the base apparatus of the most varied type.

Concluding, amongst others, the advantages are that a linear array may be formed from ultrasonic sensor modules, by which means it may be adapted to the testing problems, this with regard to the distance of the modules, the number of the modules, the number of averages per measurement, the transmitter pulse shape. Testing heads with tip contact are used, by which means no coupling medium is necessary. All sensor modules measure in a parallel manner, and have integrated electronics and carry out an analog-to-digital conversion of the measurement signals. Several measurements may be added and stored in the memory of the sensor modules. The data from the memory of the sensor modules is read out via a data bus to the base apparatus.

It is possible by way of the device according to the invention, to carry out the desired ultrasonic examinations in quasi real-time, i.e. in less than one second, and to represent these.

BRIEF DESCRIPTION OF DRAWINGS

One embodiment is represented in the drawing and is explained in more detail in the subsequent description. There are shown in.

DETAILED DESCRIPTION

Figure 1:
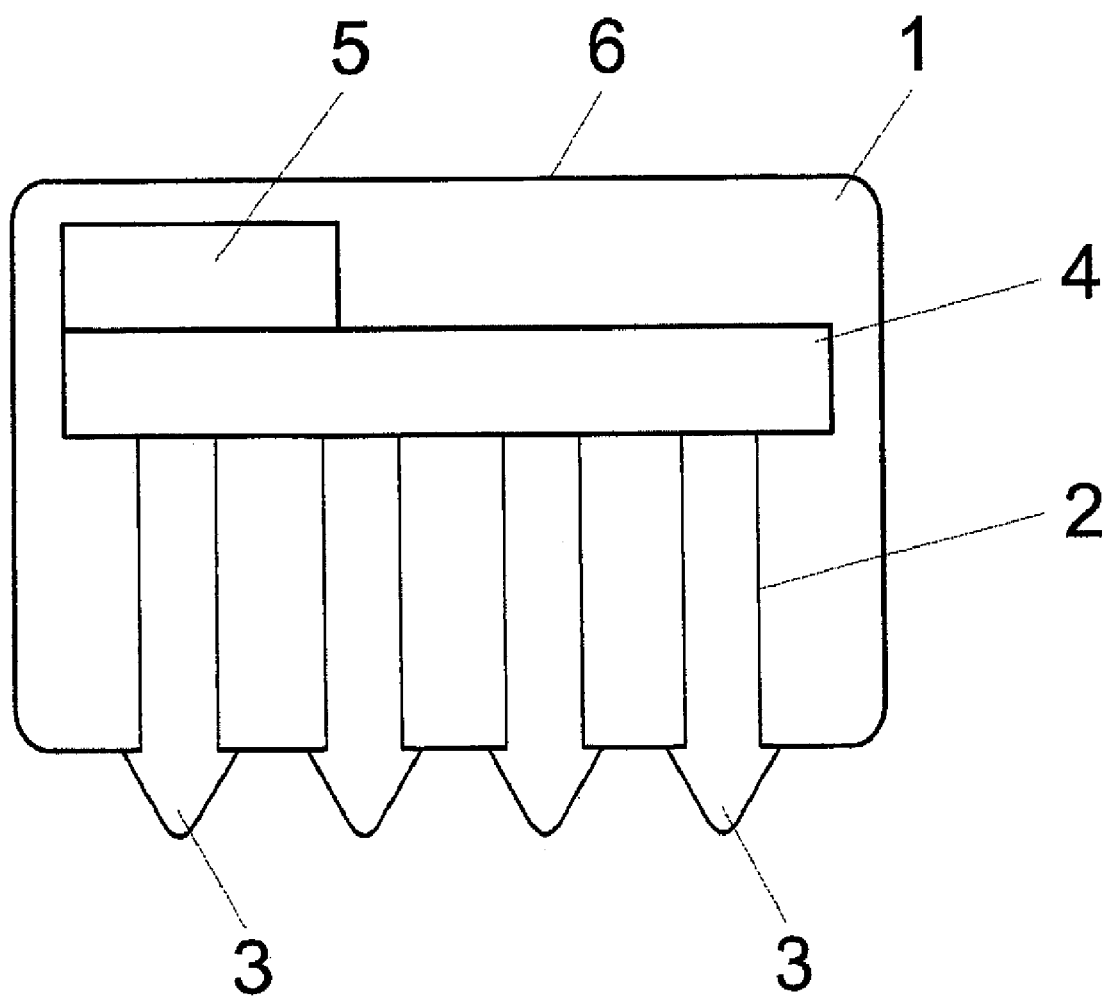
FIG. 1 a schematic representation of the construction of the sensor module.

A sensor module 1 is represented schematically in FIG. 1, which comprises four ultrasonic testing heads 2 which are arranged in a row, parallel to one another. The ultrasound testing heads 2 for example comprise piezoelectric elements which are not represented, and which produce ultrasonic waves. Furthermore, they are provided with ceramic tips 3 which create the contact to the surface of the component to be examined. The testing heads 2 are individually mounted in resilient holders which are not shown, by which means one ensures an adaptation also to uneven surfaces. The four testing heads are connected electrically in parallel and connected to electronics 4 for activating the testing heads 2 and for reading acquisition. The electronics have a pulse shaper unit for producing transmitter pulses as well as amplifiers, filters, A/D-transducers and a memory unit, and are provided with connections 5 for the control and data bus. The ultrasonic testing heads 2 and the electronic unit 4 with the bus connections 5 are accommodated in a housing 6 which is provided with holders or plug connections which are not shown and via which the housing 6 may be connected to one or two other housings. Thereby, the distance of adjacent modules is the same and may be set in limits between 2 and 10 cm.

Figure 2:
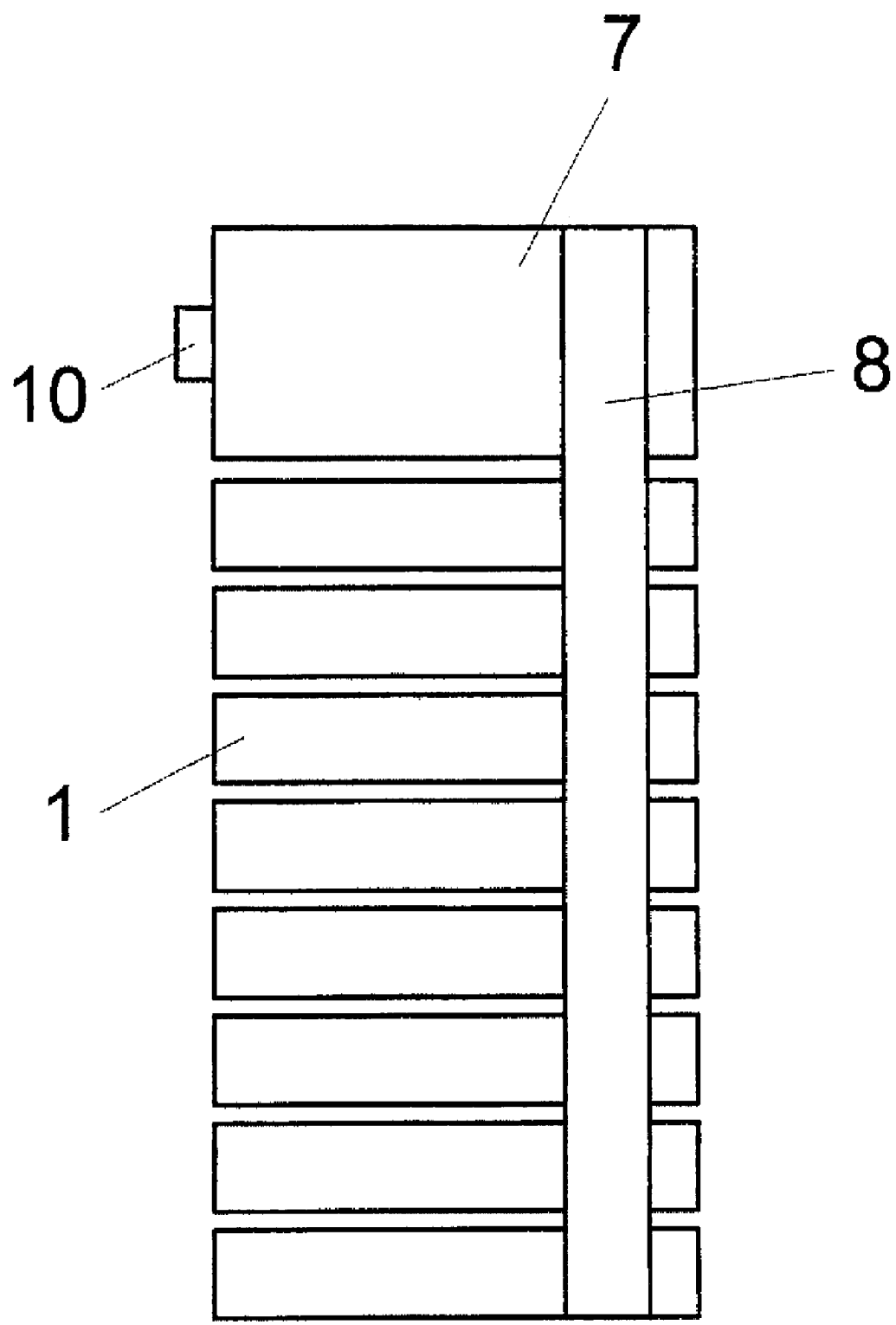
FIG. 2 a schematic representation of the complete device for the destruction-free testing.

The construction of the device for the destruction-free testing is represented schematically in FIG. 2, which is composed of a plurality of sensor modules 1 which are described above and which are connected to one another via the holder or the plug connection, and of a base apparatus 7, as well as of a bus system 8. For example, the data bus is designed in the form of a flat strip cable, and a plug is branched off for each sensor module of the array. The individual sensor modules have fixedly set hardware addresses, via which they may be inquired. The base apparatus 7 is likewise accommodated in a housing, wherein it includes a control- and evaluation device for the activation of the sensor modules or ultrasonic testing heads, and for the evaluation of the measurement data provided by the sensor modules. The base apparatus 7 is arranging locally removed from the sensor module array, and is connected to this via the bus system 8 consisting of control- and data leads. The base apparatus is furthermore provided with one or more interfaces 9 as are generally known (USB, Fire-Wire, serially, wireless LAN, Bluetooth). If the sensor modules are connected, the base apparatus recognizes that a module has been added, and configures it accordingly. It may be used as a transmitter- and as a receiver sensor and is switched over between these conditions by the base apparatus.

The axis through the test heads of the sensor modules 1 is directed perpendicularly to the axis of the linear array 9. A measurement is activated by a start signal from the base apparatus 7 via the bus 8, after the sensor module array 9 has been brought into position on the component to be examined.

The bringing into position may be carried out for example by way of a positioning vehicle, which carries the array 9 and is lowered on the measurement locations, and the sensors are mechanically pressed upon. The measurement is triggered by a start signal from the base apparatus 7, by which means the sensor module defined as a transmitter module produces transmitter pulses, wherein the shape of the transmitter pulses may be set in a manner adapted to the problem, and after a selectable delay after the start signal, they are fed into the component. The receiver modules detect the ultrasonic signals present on account of scattering and reflection, and lead them further to the electronic unit 4 of each receiver module, which filters and amplifies the signals and carries out an analog-digital conversion. The result of the conversion is written in a memory, and if several repetitions of the measurements are carried out within a measurement sequence for improving the signal-to noise ratio, the results may be added up in the memory, and averaged as the case may be, or also stored in a separate manner. After a measurement sequence, the data is read out of the modules 1 and transmitted via the control- and data leads 8 to the base apparatus 7, on the command of the base apparatus 7. The evaluation unit present in the base apparatus may for example carry out an imaged reconstruction of the component for example with the help of a SAFT algorithm, and transmit the respective data via the interface 10. It is also possible to deliver the data of all sensor modules, which is stored in the base apparatus 7 in a memory, via an interface 10 to an external evaluation device 8.

The invention claimed is:

1. A device for the destruction-free testing concrete components with ultrasound, comprising:
    at least one sensor module with several ultrasonic testing heads functioning as transmitters and/or receivers;
    a device for producing transmitter impulses for ultrasonic radiation provided with the sensor module; and
    a device for acquiring ultrasonic readings provided with the sensor module,
    wherein several sensor modules for forming an array are mechanically connected to one another, and wherein a control and evaluation device for activating the sensor modules with their ultrasonic heads, and for evaluation of the readings delivered by the sensor modules is connected via a bus system with control and data leads to the sensor modules, and the control and evaluation device is designed in a manner such that it recognizes the respective sensor module on joining together into the array, and configures and activates it, as a transmitter sensor or a receiver sensor.

2. A device according to claim 1, wherein the testing heads of each sensor module are individually mounted in resilient holders, and are provided with contacts, having ceramic tips.

3. A device according to claim 1, wherein the testing heads of each sensor module are arranged linearly in a row, and are accommodated in a module housing.

4. A device according to claim 1, wherein the sensor modules are mechanically and/or electrically joined to one another into the array in a releasable manner by way of a holder, having a plug connection.

5. A device according to claim 1, wherein the device for producing transmitter impulses of the transmitter module is designed in a manner such that the testing heads operate in transversal wave operation or longitudinal wave operation.

6. A device according to claim 5, wherein a switch-over between the operating modes is provided.

7. A device according to claim 1, wherein the control and evaluation device is designed to issue a start signal for the beginning of a measurement sequence to the sensor modules via the control and data bus, wherein at least one sensor module may be defined as an transmitter module and the others as receiver modules.

8. A device according to claim 1, wherein the device for acquiring the readings of each sensor module comprises an amplifier, an A/D-transducer and a memory, wherein the received data of a measurement sequence detected by the testing heads serving as receivers, and converted, is stored in the memory.

9. A device according to claim 8, wherein after completion of the measurement sequence, the stored data may be transmitted via the data bus to the control- and evaluation device.

10. A device according to claim 1, wherein the control and evaluation device is accommodated in a housing, for forming a base apparatus.

11. A device according to claim 10, wherein the base apparatus is provided with at least one interface for data transmission.

12. A device according to claim 1, wherein the control- and evaluation device carries out an evaluation of the measurement data on the basis of the SAFT algorithm for providing a three-dimensional picture.

* * * * *